(12) United States Patent
Lee et al.

(10) Patent No.: US 7,923,551 B2
(45) Date of Patent: Apr. 12, 2011

(54) METHOD OF PURIFYING RNA USING KOSMOTROPIC SALT

(75) Inventors: Myo-yong Lee, Suwon-si (KR); Nam Huh, Seoul (KR); Joon-ho Kim, Seongnam-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 354 days.

(21) Appl. No.: 12/110,391

(22) Filed: Apr. 28, 2008

(65) Prior Publication Data

US 2009/0048437 A1 Feb. 19, 2009

(30) Foreign Application Priority Data

Aug. 16, 2007 (KR) .................. 10-2007-0082277

(51) Int. Cl.
*C07H 21/00* (2006.01)
(52) U.S. Cl. .................. 536/25.4; 536/25.41; 536/25.42

(58) Field of Classification Search .................. None
See application file for complete search history.

(56) References Cited

U.S. PATENT DOCUMENTS

| | | |
|---|---|---|
| 5,234,809 A | 8/1993 | Boom et al. |
| 2006/0270031 A1 | 11/2006 | Hwang et al. |
| 2007/0043216 A1 | 2/2007 | Bair, Jr. et al. |
| 2007/0092403 A1 * | 4/2007 | Wirbisky et al. .................. 422/65 |
| 2007/0238109 A1 | 10/2007 | Min et al. |
| 2007/0269819 A1 | 11/2007 | Kim et al. |

* cited by examiner

*Primary Examiner* — Patrick T Lewis
(74) *Attorney, Agent, or Firm* — Sughrue Mion, PLLC

(57) ABSTRACT

The present invention provides a method of purifying RNA, including contacting a solid support with an acidic solution having a RNA-containing sample and a kosmotropic salt having a concentration of less than 1M, thereby binding the RNA to the solid support. According to the present invention, RNA is purified efficiently due to high RNA yield and low contamination by DNA. The present invention is particularly effective in purifying RNAs of 200 nucleotides or less.

17 Claims, 8 Drawing Sheets

METHOD OF PURIFYING RNA USING KOSMOTROPIC SALT

CROSS-REFERENCE TO RELATED PATENT APPLICATION

This application claims the benefit of Korean Patent Application No. 10-2007-0082277, filed on Aug. 16, 2007, in the Korean Intellectual Property Office, the disclosure of which is incorporated herein in its entirety by reference.

BACKGROUND OF THE INVENTION

1. Field of the Invention

The present invention relates to a method of purifying RNA using a kosmotropic salt, and more particularly, to a method of purifying a RNA molecule from a biological material including the RNA using a kosmotropic salt on a solid support.

2. Description of the Related Art

A conventional method of separating RNA from a starting material containing the RNA includes guanidinium thiocyanate-phenol-chloroform extraction (so-called Trizol method). In the Trizol method, cells are added into a mixed solution of phenol and guanidine isothiocyanate to lyse the cells, and chloroform is added to the resulting cell lysate to separate the lysate into an aqueous layer and an organic layer, where RNA is in the aqueous layer, protein is in the organic layer, and DNA is at the interface between the aqueous layer and the organic layer. The aqueous layer is then treated with isopropanol.

According to another method for separating RNA, which is disclosed in U.S. Pat. No. 5,234,809, cells are mixed with a chaotropic substance (i.e. a substance which alters the secondary, tertiary and/or quaternary structure of proteins and nucleic acids, but leaving at least the primary structure intact) and a nucleic acid-binding solid phase to produce solid phase-nucleic acid complexes, and the nucleic acid is eluted from the complexes. As chaotropic substance guanidine isothiocyanate or guanidine hydrochloride, sodium iodide may be used and as the solid phase, silicate particles are used.

The methods described above not only use hazardous materials such as phenol, chloroform, and isothiocyanate (which is a chaotropic material), but the RNA obtained contains large amounts of DNA contaminants. Chaotropic materials are known to dehydrate a silica surface to allow nucleic acids to bind to the silica surface by hydrophobic interaction.

U.S. Patent Application Publication No. 2007-0043216 A1 discloses a method of purifying RNA using a buffer (pH<4.5 or pH>7) including a 4-10M RNA-complexing salt such as LiCl, a detergent, and a solid support. The buffer lacks a chaotrope.

SUMMARY OF THE INVENTION

The present invention provides a method of purifying RNA using a kosmotropic salt on a solid support.

There is provided a method of separating a RNA molecule from a material containing the RNA molecule ("RNA molecule-containing material"), including steps of bringing an acidic solution ("binding solution"), which comprises a kosmotropic salt and the RNA molecule-containing material to be in contact with a solid support, to allow the RNA molecule to bind to the solid support; and separating the solid support to which the RNA molecule is bound ("RNA molecule-bound support"), wherein the concentration of the kosmotropic salt in the binding solution is less than or equal to about 1M.

According to an embodiment, the kosmotropic salt may be a salt formed from an anion selected from the group consisting of a sulfate ($SO_4^{2-}$), a phosphate ($HPO_4^{2-}$), an acetate ($CH_3COO^-$), a hydroxide ($OH^-$), a chloride ($Cl^-$), and a formate ($HCOO^-$).

In the method, the concentration of the kosmotropic salt may be 0.3M-0.9M and the binding solution may have the pH ranging from 3 to 6.

In an embodiment, the RNA molecule has about 200 nucleotide residues or less.

According to another embodiment, there is provide a method of separating a RNA molecule from a material containing the RNA molecule ("RNA molecule-containing material"), including the steps of bringing a solution of a kosmotropic salt, the RNA molecule-containing material, and a solid support to be in contact each other, to allow the RNA molecule to bind to the solid support, wherein the pH of a resulting mixture of the solution of the kosmotropic salt and the RNA molecule-containing material is adjusted to be in the range of 3-6, if the pH of the resulting mixture is not in such range; and separating the solid support to which the RNA molecule is bound ("RNA molecule-bound support"), wherein the kosmotropic salt excludes magnesium sulfate and magnesium chloride, and the concentration of the kosmotropic salt in the solution is less than or equal to about 1M.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1A:
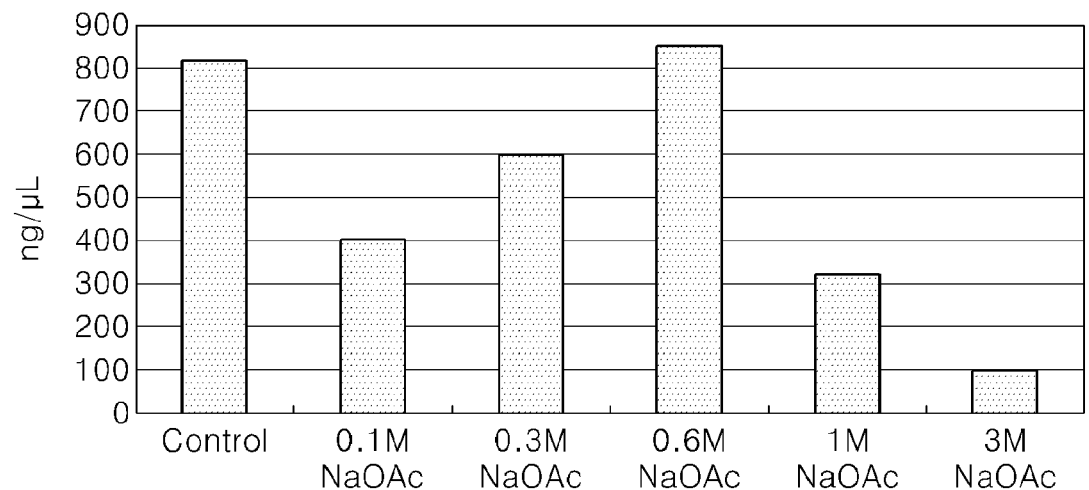
FIG. 1A is a graph representing RNA yields when $CH_3COONa$ was used in the contacting step of the method of purifying RNA according to an embodiment of the present invention.

Hereinafter, the present invention will be described more fully, including with reference to the accompanying Examples, in which exemplary embodiments of the invention are shown. The terms "kosmotrope" or "kosmotropic" (order-maker) and "chaotrope" or "chaotropic" (disorder-maker) are generally used to denote solutes that stabilize or destabilize, respectively, proteins and membranes. Later they referred to the apparently correlating property of increasing, or decreasing respectively, the structuring of water. The term "kosmotropic salt" as employed herein indicates a salt, which has ability to increase water structure. In particular, the salt is formed of an ion which has the same degree of effects on the solubility of a protein in a given solution as kosmotropic ions of Hofmeister series do, and its counterion.

The Hofmeister series is a classification of ions in order of their ability to change water structure. Anions series is as follows: $SO_4^{2-} < HPO_4^{2-} < OH^- < F^- < HCOO^- < CH_3COO^- < Cl^- < Br^- < NO_3^- < I^- < SCN^- < ClO_4^-$. Cations series is: $NH_4^+$, $Rb^+$, $K^+$, $Na^+$, $Cs^+$, $Li^+$, $Ca^{2+}$, $Mg^{2+}$, and $Ba^{2+}$. However, magnesium sulfate and magnesium chloride are excluded from the present invention. The inventors found that magnesium sulfate and magnesium chloride unexpectedly do not retain the kosmotropic characteristics. Examples of kosmotropic ions are not limited to those listed in Hofmeister series. Anions or cations having the same degree of effects on secondary and/or tertiary structures of a protein under the same condition to a sulfate ($SO_4^{2-}$), phosphate ($HPO_4^{2-}$), acetate ($CH_3COO^-$), hydroxide ($OH^-$), chloride ($Cl^-$), or formate ($HCOO^-$) may be used. In Hofmeister series, the chaotropic salts randomize the structure of the liquid water and thus tend to decrease the strength of hydrophobic interactions. In contrast, the kosmotropic salts promote hydrophobic interactions and protein precipitation, due to the higher 'salting-out' or molal surface tension increment effects. Quantification of the Hofmeister (solubility) effect of a salt is usually obtained via linear regression of the relative solubility of a chosen solute (e.g., proteins, peptides, or simple organic molecules) versus the salt's concentration. See for example, E. Leontidis, Hofmeister anion effects on surfactant self-assembly and the formation of mesoporous solids, Current Opinion in Colloid & Interfaces Science 7 (2002) 8191; M. G. Cacace et al., The Hofmeister series: salt and solvent effects on interfacial phenomena, Quarterly Reviews of Biophysics 30 (1997) 241-277; A. S. Thomas and A. H. Elcock, Molecular dynamics simulations of hydrophobic associations in aqueous salt solutions indicate a connection between water hydrogen bonding and the Hofmeister effect, JACS 129 (2007) 14887-14898.

According to an embodiment of the present invention, there is provided a method of separating RNA molecule from a RNA molecule-containing sample, including contacting a solid support with an acidic solution having the RNA molecule-containing sample and a kosmotropic salt, wherein the concentration of the kosmotropic salt is less than or equal to 1M in the solution, thereby allowing the RNA molecule to be bound to the solid support.

The present invention includes binding a RNA molecule to a surface of the solid support using a kosmotropic salt solution. The bound RNA molecule may be separated from the solid support by adding a low concentration salt solution to elute the RNA molecule from the solid support. Conventional RNA separation techniques use chaotropic salts or a solution including an RNA-complexing salt, such as 4-10M LiCl. The method of the present invention can be used to effectively purify a RNA molecule while minimizing DNA contamination, by using a kosmotropic salt. The method according to the present invention may be applicable to single stranded RNA molecules as well as double stranded RNA molecules. The method of the present invention is also effective in purifying RNAs having sizes of less than or equal to about 200 nucleotides. The inventors speculate that kosmotropic salts hydrate the surface of the solid support, allowing RNA molecules to bind to the surface of the solid support.

Examples of the kosmotropic salts which can be employed in the present invention include, but not are not limited to, those listed in Hofmeister series (excluding magnesium sulfate and magnesium chloride), in particular a salt composed of $SO_4^{2-}$, $HPO_4^{2-}$, $OH^-$, $F^-$, $HCOO^-$, $CH_3COO^-$, $Cl^-$, $NH_4^+$, $Rb^+$, $K^+$, $Na^+$, $Cs^+$, $Li^+$, $Ca^{2+}$, $Mg^{2+}$, and $Ba^{2+}$, and a counter ion thereof. In embodiments of the present invention, NaCl, $(NH_4)_2SO_4$, $Na_2SO_4$, or NaOAc may be used.

The method of separating a RNA molecule according to an embodiment of the present invention may further include washing the RNA molecule-bound solid support to remove non-bound RNA molecules and other substances contained in the sample, in order to increase the purity of separated RNA molecules. A solution used for binding the RNA molecule to the solid support may be used as a wash solution. In one embodiment, the RNA-bound solid support may be washed primarily with a first wash solution which is the same solution to the binding solution and includes a kosmotropic salt in the concentration of less than or equal to 1M (but lacks the RNA-containing sample), then washed secondarily with a second wash solution, which is the same to the binding solution, but adjusted to have neutral pH of about 6 to about 9. The first wash solution may further include an alcohol. The alcohol may be a lower alcohol of 1-6 carbon atoms.

The method of separating a RNA molecule according to the current embodiment of the present invention may further include applying an RNA-eluting solution to the RNA-bound solid support to elute the RNA from the solid support. Even though the RNA molecules can be used as they are bound to the solid support, it may be convenient and efficient to use free purified RNA molecules for subsequent processes such as reverse transcription, amplification, and analysis. The RNA-eluting solution may be water or an aqueous solution containing a salt of 10 mM or less.

In the method of separating and purifying RNA according to the current embodiment of the present invention, the kosmotropic salt may contain a sulfate ($SO_4^{2-}$), a phosphate ($HPO_4^{2-}$), an acetate ($CH_3COO^-$), a hydroxide ($OH^-$), a chloride ($Cl^-$), or a formate ($HCOO^-$), but is not limited thereto.

In the method of separating and purifying RNA according to the current embodiment of the present invention, the pH of the solution including the kosmotropic salt and the RNA-containing sample ("binding solution") may be an acidic pH. In one embodiment, the pH of the binding solution is in the range of from about 3 to about 6. In the method of separating and purifying RNA according to the current embodiment of the present invention, the concentration of the kosmotropic salt may be less than or equal to about 1M, and preferably 0.3M-0.9M.

In the method of purifying RNA according to the current embodiment of the present invention, the solid support may be formed of silica, glass, silicon wafer, magnetic material, polystyrene, film, metal, or metal oxide including alumina, but is not limited thereto. Moreover, in the case where the solid support has a flat structure or shape, such as glass slide or silicon wafer, the surface of the solid support may be processed to form a pillar in order to expand the surface area of the solid support. The surface of the solid support may have a shape a slide, pillar, bead, or sieve.

In the method of according to the current embodiment of the present invention, the RNA-eluting solution may be a known buffer such as phosphate, Tris, HEPES ((4-(2-hydroxyethyl)-1-piperazineethanesulfonic acid), CHES (N-Cyclohexyl-2-aminoethanesulfonic acid), or borate, but is not limited thereto. The RNA-eluting buffer may have a salt in the concentration of 10 mM or less.

In the method according to the current embodiment of the present invention, the RNA-eluting solution may have a pH of 4-10. When the pH is outside the above range, the RNA molecule may be disintegrated and/or the subsequent process to be performed on the separated/purified RNA molecule may be influenced by the disintegrated RNA molecule.

In the method according to the current embodiment of the present invention, the RNA binding to or elution from the solid support may be performed under static or fluidic conditions. The RNA and the solid support may be put into contact with each other under a static condition, but it is also possible to put them into contact with each other under a fluidic condition. That is, the RNA-containing solution is allowed to move freely in a fluid control system, during which RNA molecules in the solution bind to the solid support. In the fluid control system, the solid support may have a flat surface or have a flat slide shape, but in order to increase the frequency of the contact between the nucleic acids and the solid support and, thus, increase the recovery of the nucleic acids, the surface of the solid support may be in the form of pillars.

In the method according to the current embodiment of the present invention, the RNA-containing sample may be blood, serum, urine, saliva, ocular lens solution, cerebrospinal fluid, milk, ascetic fluid, synovial fluid, peritoneal cavity fluid, amniotic fluid, tissue, fermentation broth, cell culture solution, PCR product, or nucleic acid synthesis product, but is not limited thereto. The RNA containing sample of the present invention may be derived from mammals, plants, bacteria, or yeast. The sample may have a single-cell form, or a tissue form, and the cells or tissue may be derived from an in vitro culture.

The purified RNA using the method according to the present invention may be subjected to subsequent process, for example analysis for molecular weight by electrophoresis, or nucleotide base sequencing.

Other subsequent processes include reverse transcription or amplification. If the amount of RNA eluted is too small to analyze directly, the RNA can be amplified using methods such as PCR (polymerase chain reaction) to more effectively detect the RNA. The RNA amplification may be performed without removing the RNA elution solution.

According to another embodiment of the present invention, there is provided a RNA purifying device comprising: a solid support; and a unit which stores a solution containing a kosmotropic salt, wherein the unit is connected with the solid support through a microchannel, and supplies the kosmotropic salt to a compartment where the solid support is placed or provided.

The RNA purifying device according to the current embodiment of the present invention is composed of a kosmotropic salt solution storing unit and a solid support. The kosmotropic salt solution storing unit supplies a kosmotropic salt to the solid support, and is connected with the solid support by a first microchannel. When a sample containing a RNA molecule to be separated is introduced into the RNA purifying device, the kosmotropic salt is supplied to the solid support from the kosmotropic salt solution storing unit. The RNA-containing sample and the kosmotropic salt are then mixed in the RNA purifying device and the RNA binds to the solid support. In order to elute the bound RNA, the RNA purifying device may further include an RNA-eluting solution storing unit which is connected with the solid support through a second microchannel, and supplies RNA-eluting solution to the solid support.

In the RNA purifying device according to the current embodiment of the present invention, the solid support may be a slide glass, silicon wafer, magnetic material including magnetic beads, polystyrene, membrane, or metal oxide including alumina, but is not limited thereto. Moreover, in the case where the solid support is a flat support, such as slide glass or wafer, the surface of the solid support may be processed to form pillars or protrusions in order to increase the surface area of the solid support. The solid support may be in the form of a flat slide, rough surfaced slide, bead, or sieve.

In the RNA purifying device according to the current embodiment of the present invention, the kosmotropic salt may be a salt of anions such as sulfate ($SO_4^{2-}$), a phosphate ($HPO_4^{2-}$), an acetate ($CH_3COO^-$), a hydroxide ($OH^-$), a chloride ($Cl^-$), or a formate ($HCOO^-$), but is not limited thereto.

The RNA purifying device according to the current embodiment of the present invention may further include post-purification process units such as a reverse-transcription unit, a nucleic acid amplification unit, and a detection unit. The nucleic acid amplification unit may be used to amplify nucleic acids whose quantity is too small to detect directly, using a PCR device or the like. The RNA detection unit may be used to identify the presence of eluted RNA, using an electrophoresis device, a nucleotide base sequencer or the like.

According to another embodiment of the present invention, there is provided a lab-on-a-chip including the RNA purifying device described above. The RNA purifying device according to the present invention can not only be applied into a process-on-a-chip using a known microfluidics technology and a MEMS (microelectromechanical system) device, but may further be applied into a lab-on-a-chip.

According to the present invention, in the case where RNA is purified using an acidic solution containing a kosmotropic salt in a concentration of 1M or less, the RNA purification efficiency is significantly improved. The present invention is particularly effective in purifying RNAs having a size of about 200 nucleotide residues or less.

The present invention will now be described in more detail with reference to the following examples. However, these examples are for illustrative purposes only and are not intended to limit the scope of the invention.

EXAMPLE 1

Yield of RNA Purification Using a Kosmotropic Acetate

According to the provided protocol from Qiagen™ kit (RNeasy™ Protect Bacteria Mini Kit), *E. coli* was treated with lysozyme and proteinase K to produce a *E-coli* lysate.

200 µl of the *E. coli* lysate ($1 \times 10^8$~$7.5 \times 10^8$ *E. coli* cells lysed) and 1 mL sodium acetate (NaOAc) were mixed by vigorous vortexing, such that the mixed solution had a sodium acetate concentration of 0.1M (based on NaOAc), 0.3M, 0.6M, 1M, or 3M, and its pH is adjusted to 4 by adding glacial acetic acid. 600 µl of the mixed solution was placed in a Qiagen™ kit column (Qiagen RNeasy™ Mini spin column, silica gel membrane column) and centrifuged at 8000 g for 15 seconds. After washing the column with 700 µl of 1 mM NaOAc containing 3 mM of NaCl, and 500 µl of 25 mM Tris buffer (pH 7) including 80% ethanol twice, the column was centrifuged for 2 minutes at 8000 g. After transferring the column to a new 1.5 mL Eppendorf tube, 50 µl of DEPC (diethylpyrocarbonate)-treated water was added to the column and centrifuged at 8000 g for 1 minute to elute the RNA. Lap Chip™ (Agilent Co., USA) was used to determine the quantity of the RNA in the RNA eluate (See FIG. 1A). In each of the diagrams and tables, the control group shows the result of the RNA separated according to the protocol provided by the Qiagen Kit™. The control group experiments were conducted in the same manner with the experiment groups except that they used guanidine thiocyanate, i.e., a component of buffer RLT in the Qiagen Kit™, and ethanol as chaotropic binding solution and Buffer RW1 and Buffer RPE in the Qiagen Kit™ as washing solution, instead of kosmotropic salt solution. Buffer RW1 and Buffer RPE contains ethanol. Briefly, the control experiment was conducted as follows: 200 µl of the *E. coli* lysate ($1 \times 10^8$~$7.5 \times 10^8$ *E. coli* cells lysed) and 700 µl of Buffer RLT containing guanidine thiocyanate were mixed by vigorous vortexing, and the 500 µl of ethanol was added to the resultant mixture and mixed by pipetting. 700 µl of the mixed solution was placed in a Qiagen™ kit column (Qiagen RNeasy™ Mini spin column, silica gel membrane column) and centrifuged at 8000 g for 15 seconds. After washing the column with 700 µl of Buffer RW1, 500 µl Buffer RPE, and 500 µl Buffer RPE, respectively, the column was centrifuged for 2 minutes at 8000 g. After transferring the column to a new 1.5 mL Eppendorf tube, 50 µl of DEPC (diethylpyrocarbonate)-treated water was added to the column and centrifuged at 8000 g for 1 minute to elute the RNA.

Figure 1B:
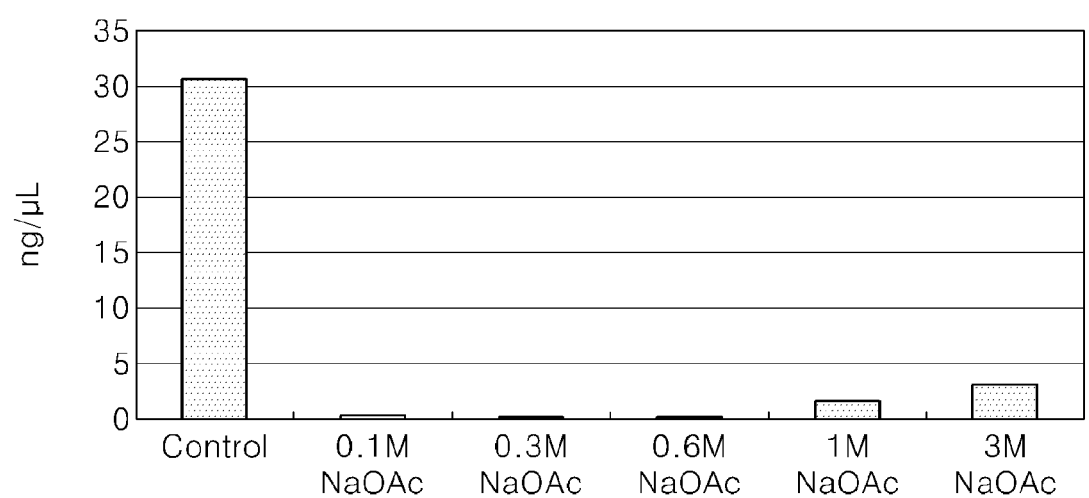
FIG. 1B is a graph showing the level of DNA contamination when $CH_3COONa$ was used as a kosmotropic salt according to an embodiment of the present invention.

The amount of the remaining DNA contaminants within the RNA eluate was quantified by PCR (LightCycler™ FastStart DNA Master SYBR Green I kit by Roche was used). A forward primer (5'-YCC AKA CTC CTA CGG GAG GC-3': SEQ. ID. NO: 1) and a reverse primer (5'-GTA TTA CCG CRR CTG CTG GCA C-3': SEQ. ID. NO: 2) pair used in the PCR amplified an area in the gDNA corresponding to 16S RNA of the *E. coli*. The PCR amplification was performed for 35 cycles, including 10 minutes of pre-denaturation at 95° C., each cycle including 5 seconds of denaturation at 95° C., 13 seconds of annealing at 62° C., and 15 seconds of extension at 72° C. The results are shown in FIG. 1B.

In addition, weight percentages of the amount of gDNA with respect to the total amount of the obtained RNA are shown in Table 1 below.

TABLE 1

| Control Group | 0.1M NaOAc | 0.3M NaOAc | 0.6M NaOAc | 1M NaOAc | 3M NaOAc |
|---|---|---|---|---|---|
| 3.79% | 0.10% | 0.03% | 0.02% | 0.53% | 3.58% |

EXAMPLE 2

Yield of RNA Purification Using a Kosmotropic Sulfate

An experiment was performed in the same manner as Example 1, except that 0.3M $Na_2SO_4$, 0.6M $Na_2SO_4$, 1M $Na_2SO_4$, 0.3M $(NH_4)_2SO_4$, 0.6M $(NH_4)_2SO_4$, and 1M $(NH_4)_2SO_4$ were used instead of the acetate salt. The above salts were dissolved in 0.1M sodium acetate buffer, pH 4.0, to produce a binding solution.

Figure 2A:
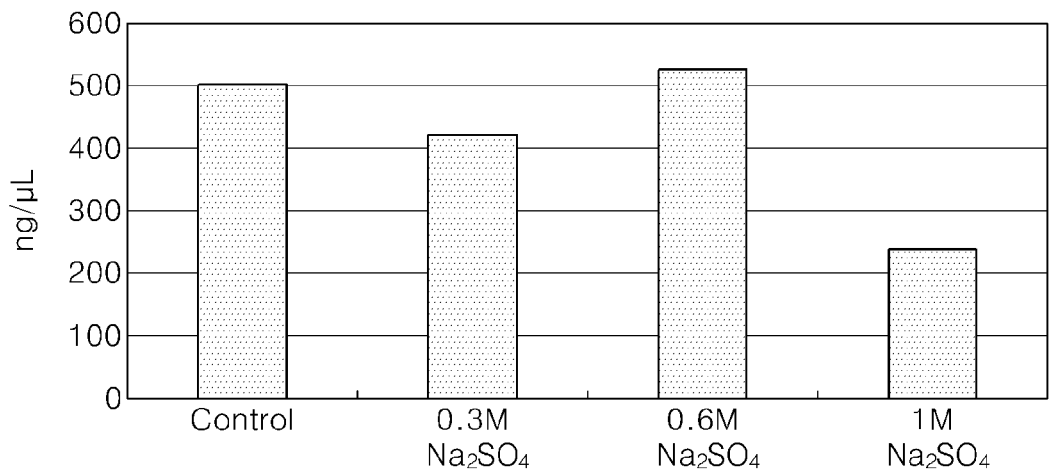
FIG. 2A is a graph showing RNA yields when $Na_2SO_4$ was used as a kosmotropic salt according to another embodiment of the present invention.
Figure 2B:
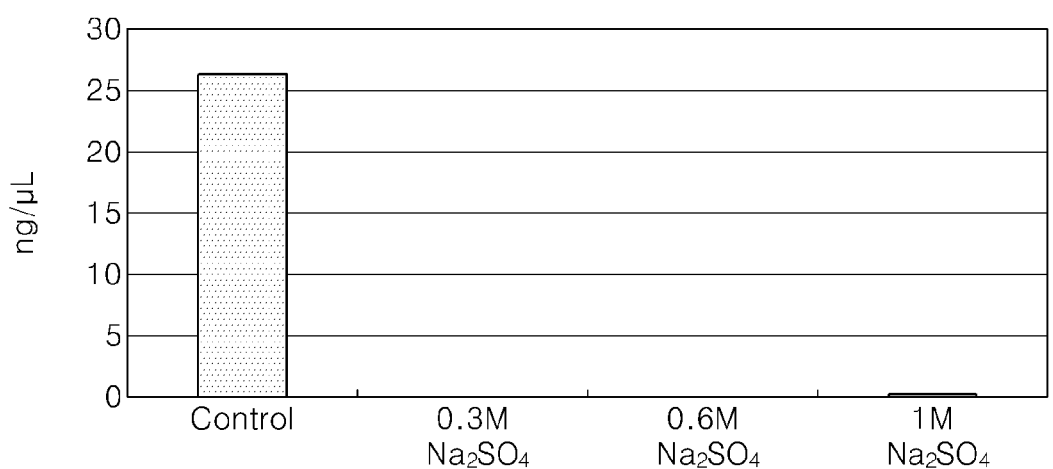
FIG. 2B is a graph showing the level of DNA contamination when $Na_2SO_4$ was used as a kosmotropic salt according the another embodiment of the present invention.

FIG. 2A and FIG. 2B shows RNA yields and the levels of DNA contamination, respectively, when $Na_2SO_4$ was used as a kosmotropic salt according to Example 2.

Figure 3A:
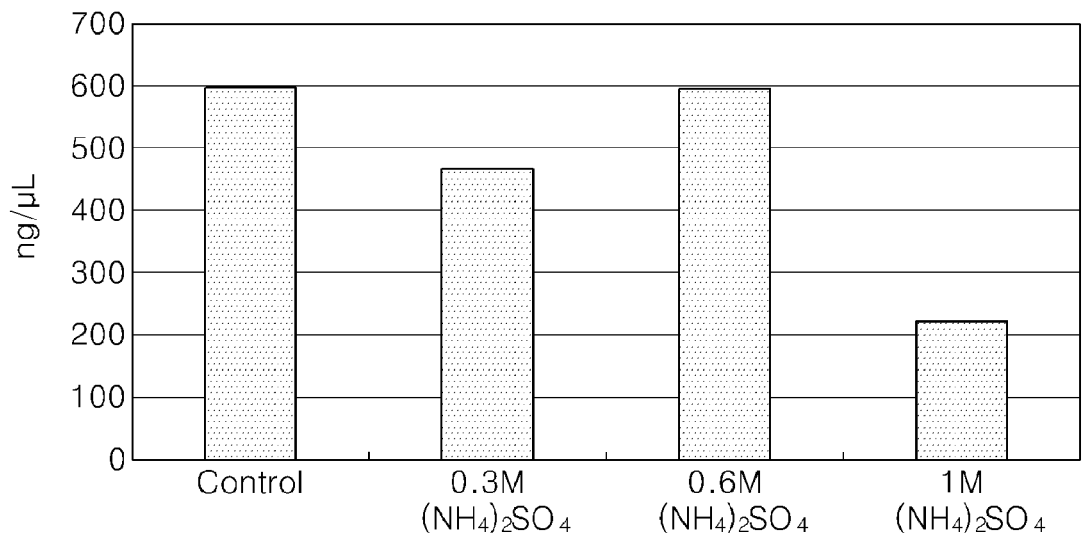
FIG. 3A is a graph showing RNA yields when $(NH_4)_2SO_4$ was used as a kosmotropic salt according to another embodiment of the present invention.
Figure 3B:
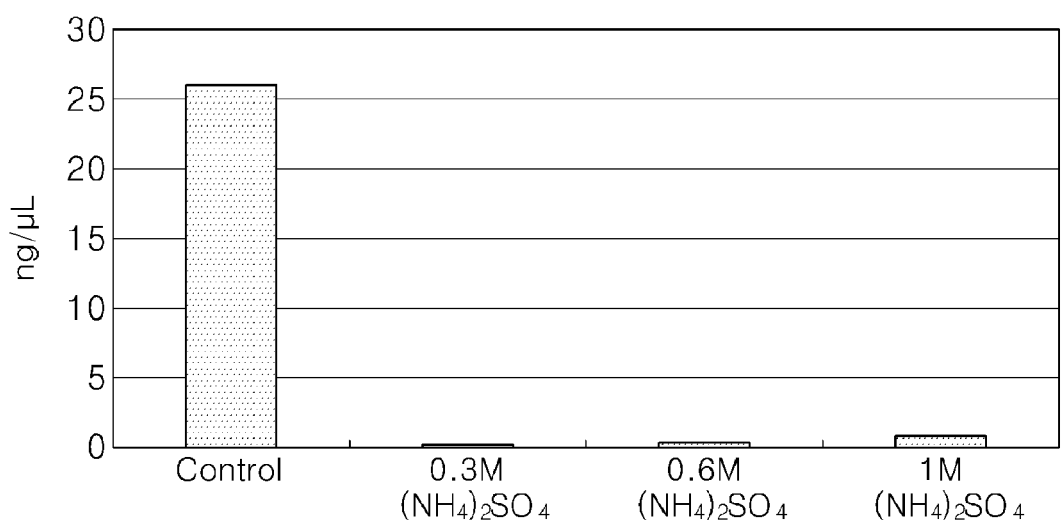
FIG. 3B is a graph showing the level of DNA contamination when $(NH_4)_2SO_4$ was used as a kosmotropic salt according to another embodiment the present invention.

FIG. 3A and FIG. 3B shows RNA yields and the levels of DNA contamination, respectively, when $(NH_4)_2SO_4$ was used as a kosmotropic salt according to Example 2.

Table 2 below shows a weight percentage of the amount of gDNA with respect to the total amount of the obtained RNA when $Na_2SO_4$ was used, and Table 3 shows weight percentages of the amount of gDNA with respect to the total amount of the obtained RNA when $(NH_4)_2SO_4$ was used as a kosmotropic salt.

TABLE 2

| Control Group | 0.3M $Na_2SO_4$ | 0.6M $Na_2SO_4$ | 1 M $Na_2SO_4$ |
|---|---|---|---|
| 5.20% | 0.02% | 0.01% | 0.04% |

TABLE 3

| Control Group | 0.3M $(NH_4)_2SO_4$ | 0.6M $(NH_4)_2SO_4$ | 1 M $(NH_4)_2SO_4$ |
|---|---|---|---|
| 4.37% | 0.04% | 0.05% | 0.39% |

EXAMPLE 3

Yield of RNA Purification Using a Kosmotropic Chloride

An experiment was performed in the same manner as Example 1, except that 0.3M NaCl, 0.6M NaCl, 1M NaCl, and 2.5M NaCl were used in place of the acetate salt, in order to provide a kosmotropic salt chloride.

Figure 4A:
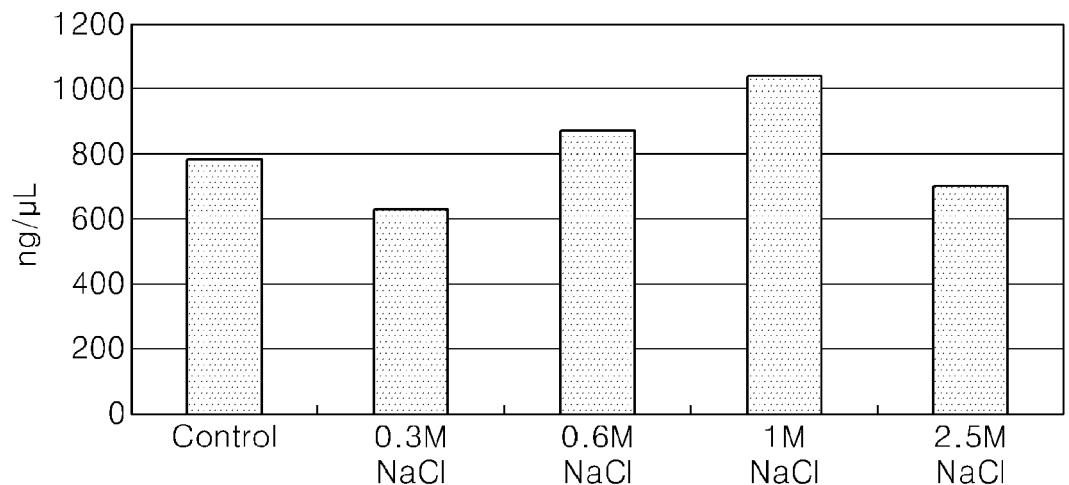
FIG. 4A is a graph showing RNA yields when NaCl was used as a kosmotropic salt according to another embodiment of the present invention.
Figure 4B:
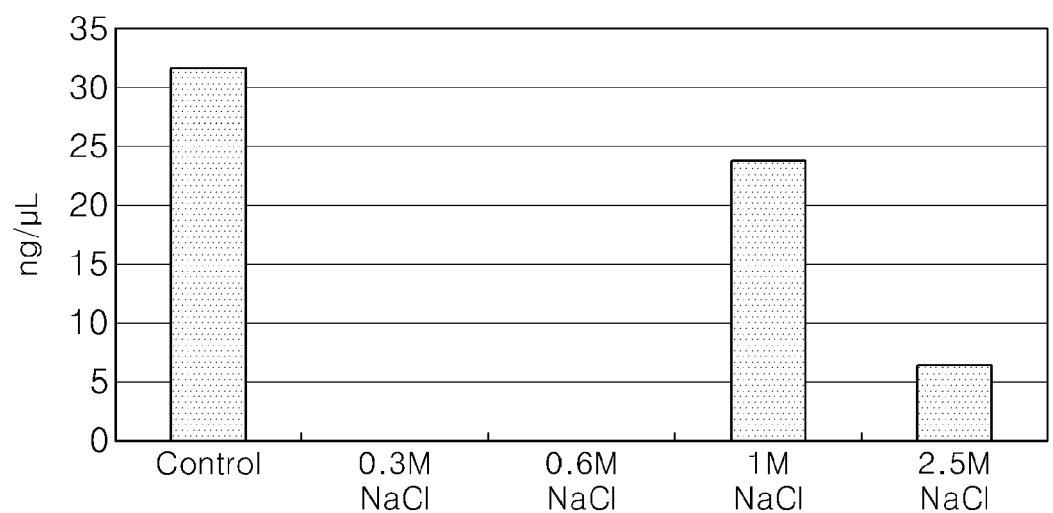
FIG. 4B is a graph showing the level of DNA contamination when $Na_2SO_4$ was used as a kosmotropic salt according to another embodiment of the present invention.

FIG. 4A and FIG. 4B shows RNA yields and the levels of DNA contamination respectively, of the purified RNA according to Example 3 when NaCl was used as a kosmotropic salt.

Table 4 below shows weight percentages of the amount of gDNA with respect to the total amount of the obtained RNA.

TABLE 4

| Control Group | 0.3M NaCl | 0.6M NaCl | 1 M NaCl | 2.5M NaCl |
|---|---|---|---|---|
| 4.050% | 0.07% | 0.005% | 2.292% | 0.942% |

Figure 5A:
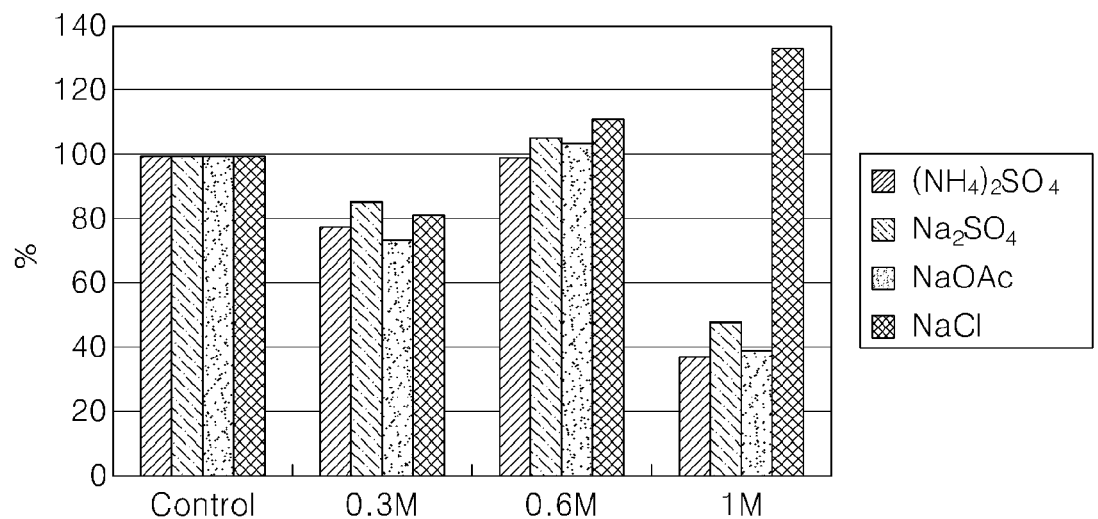
FIG. 5A is a bar graph comparing RNA yields when various kosmotropic salts—acetate, sulfate, and chloride—were used in the contacting step of the method of purifying RNA of the present invention.
Figure 5B:
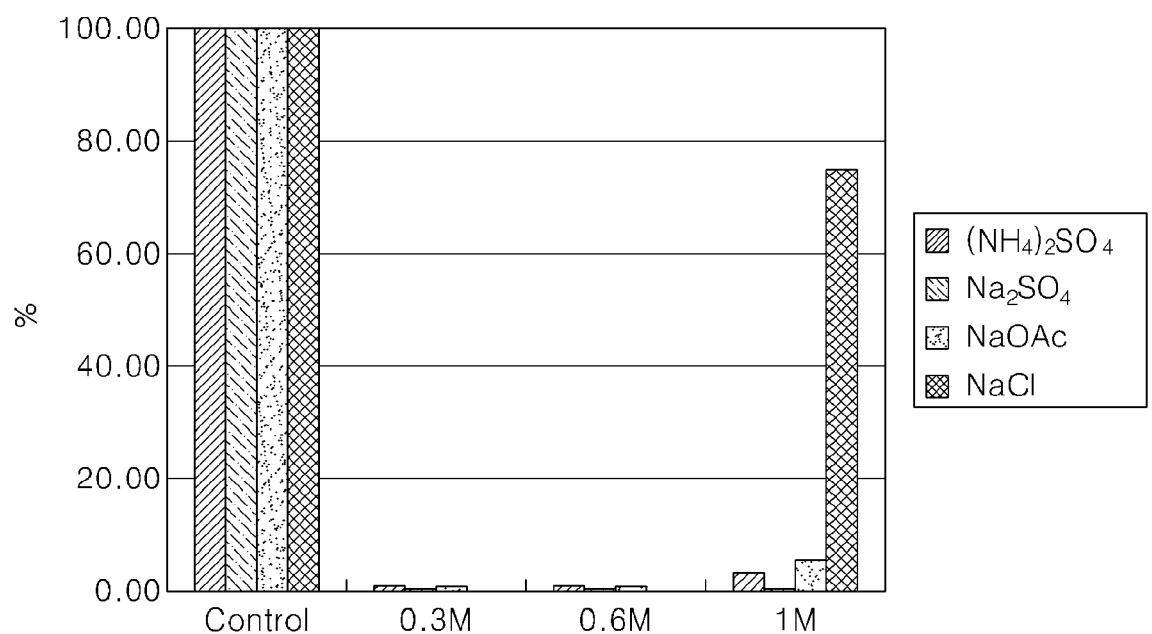
FIG. 5B is a bar graph comparing the level of DNA contamination when various kosmotropic salts—acetate, sulfate, and chloride—were used in the contacting step of the method of purifying RNA of the present invention.

FIG. 5A is a graph showing the RNA yield data obtained in Examples 2-3, each using a kosmotropic acetate, sulfate, and chloride salt, respectively, and FIG. 5B is a graph showing the levels of DNA contamination in the purified RNAs, obtained in Examples 2-3.

Generally, it can be seen that at a concentration ranging 0.3M-1M of the kosmotropic salt, the RNA yield was the highest and the DNA contamination the lowest.

EXAMPLE 4

Yield of RNA Purification According to pH

An experiment was performed in the same manner as Example 1, except that 0.6M $(NH_4)_2SO_4$ was used and the pH of the mixed solution with the *E. coli* lysate was varied. In this case, the pH of the mixed solution was adjusted by adding 0.1M sodium acetate buffer, and the pH of the wash solution was adjusted to 7.4 and pH 8.8 by adding 0.1M Tris-HCl.

Figure 6A:
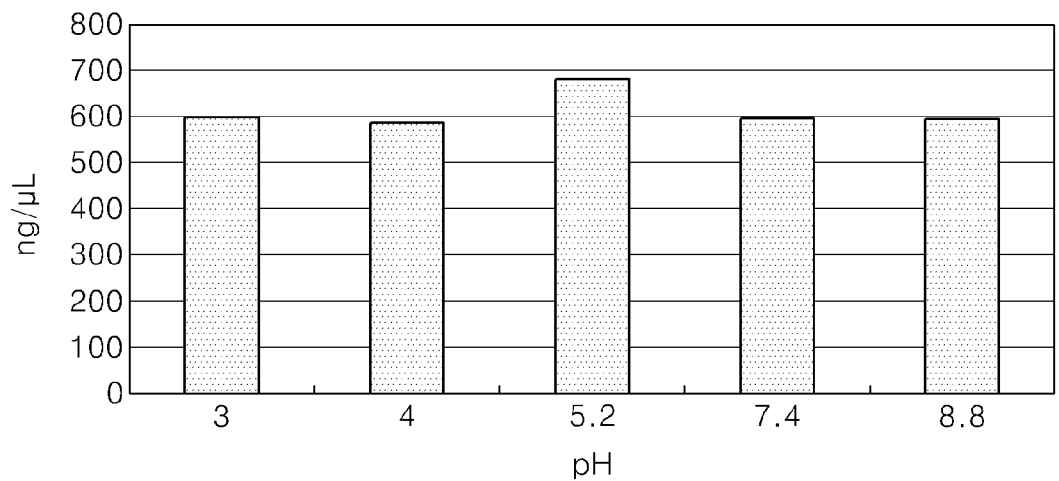
FIG. 6A is a bar graph showing RNA yields with respect to pH.
Figure 6B:
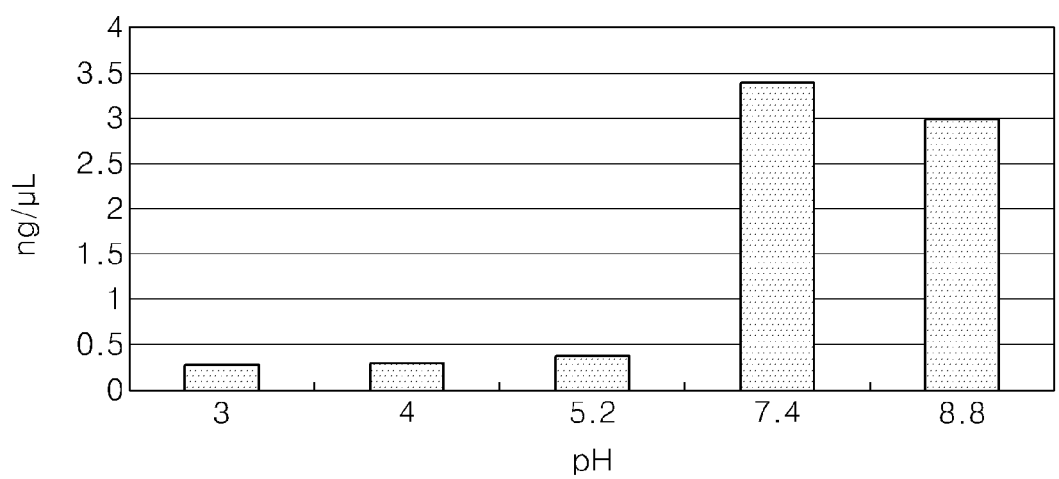
FIG. 6B is a bar graph showing the level of DNA contamination with respect to pH.

FIG. 6A shows RNA yields according to different pH in Example 4, and FIG. 6B shows degrees of DNA contamination according to different pH in Example 4.

Table 5 below shows weight percentages of the amount of gDNA with respect to the obtained RNA.

TABLE 5

| pH 3 | pH 4 | pH 5.2 | pH 7.4 | pH 8.8 |
|---|---|---|---|---|
| 0.05% | 0.05% | 0.06% | 0.57% | 0.50% |

As shown in FIGS. 6A, 6B, and Table 5, the RNA yield is high and DNA contamination is the lowest at pH 3-6.

Therefore, by using a non-hazardous kosmotropic salt, the RNA yield is comparable with that produced using a conventional method (Qiagen™ method), but the gDNA contamination is reduced several hundred-fold.

EXAMPLE 5

Purification of RNA of 200 Nucleotides or Less

An experiment was performed in the same manner as Example 1, except that 0.6M $Na_2SO_4$ was used. The separated RNA was quantified using RNA 6000 Nano Kit™ (Agilent Co., USA).

Figure 7A:
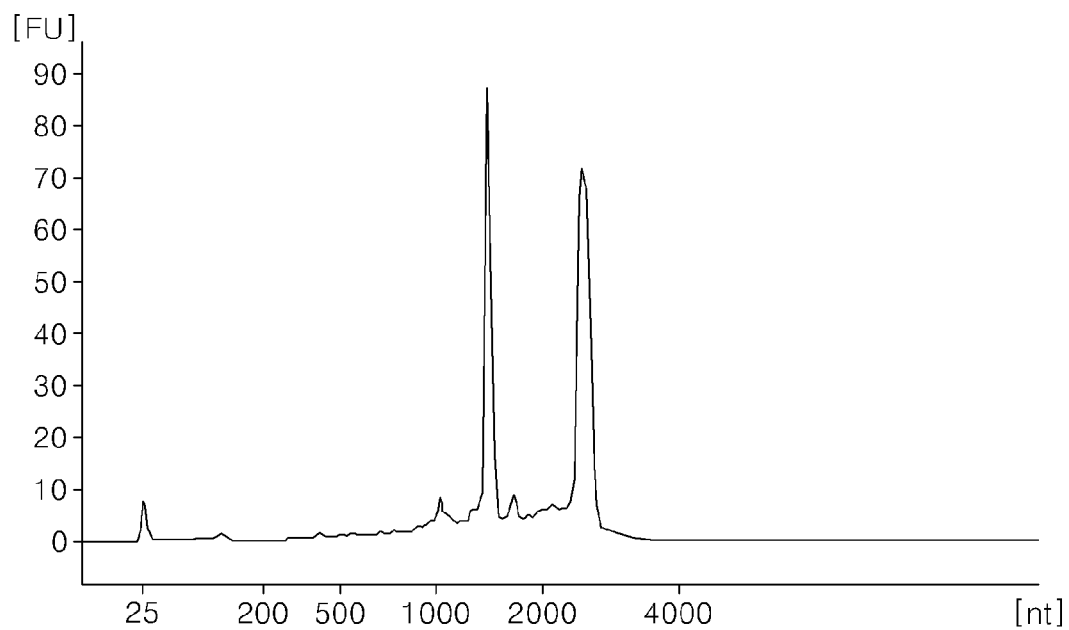
FIG. 7A is a graph showing the sizes of the RNA separated according to a conventional method, analyzed with RNA 6000 nano kit.
Figure 7B:
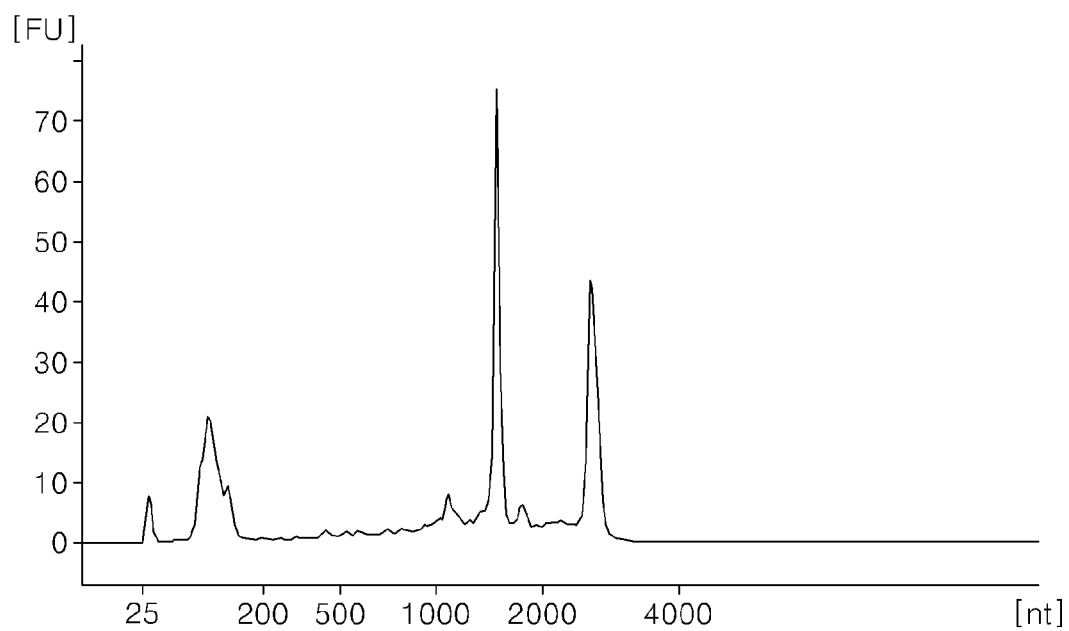
FIG. 7B is a graph showing the sizes of the separated RNA according to the present invention, analyzed with RNA 6000 nano kit.

FIG. 7A shows the results from RNA separation of the control group, and FIG. 7B shows the results from RNA separation according to the present invention. In FIGS. 7A and 7B, the peaks around 1.5 kb and 2.9 kb each represent 16S rRNA and 23S rRNA. As shown in the results of FIGS. 7A and 7B, small RNAs of 200 nucleotides or less are obtained by the RNA separation according to the present invention.

Figure 8A:
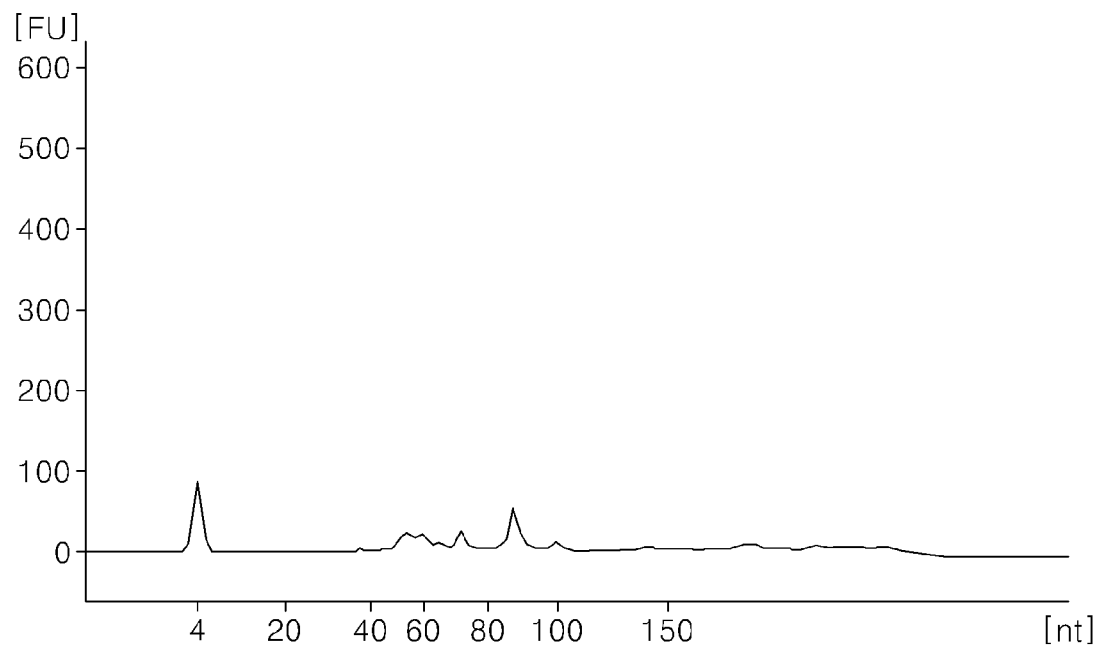
FIG. 8A is a graph representing the sizes of the RNA separated according to a conventional method, analyzed with Agilent™ Small RNA kit.
Figure 8B:
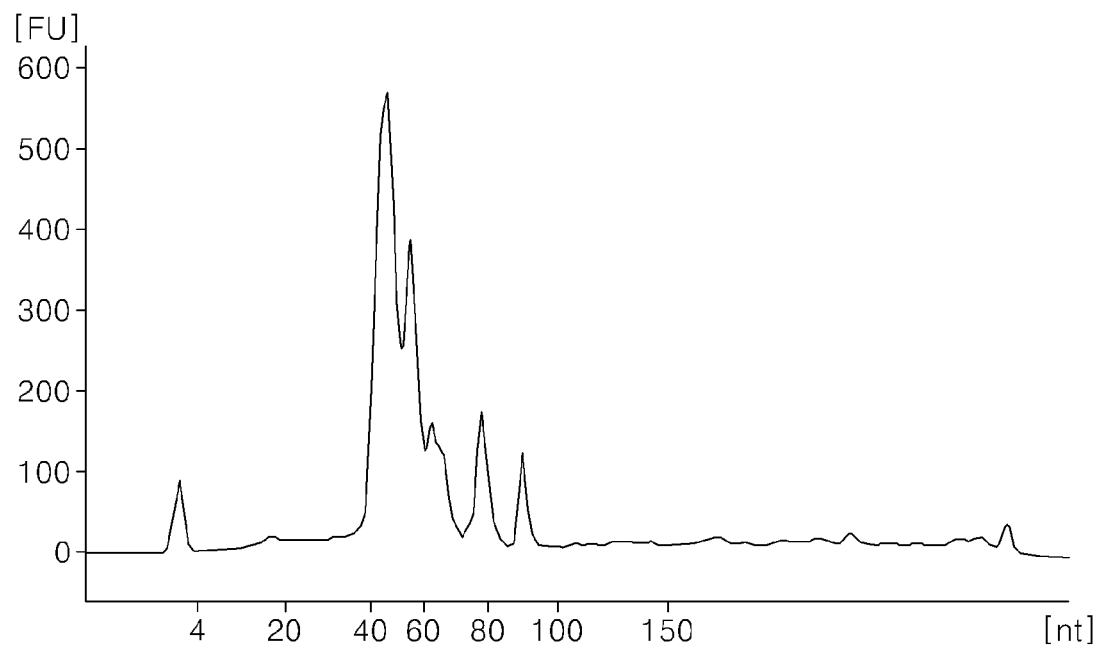
FIG. 8B is a graph representing the sizes of the separated RNA according to the present invention, analyzed with Agilent™ Small RNA kit.

In order to measure more precisely the size of the purified RNAs, an Agilent™ Small RNA kit was used. FIG. 8A shows the RNA separation results of the control group, and FIG. 8B shows the RNA separation results according to the present invention. These results show that the method according to the present invention is more effective in purifying a small RNA molecule of 200 nucleotide residues or less, compared to a conventional method.

Thus, the present invention allows an effective method for isolating and purifying RNA with minimal DNA contamination on a solid support by using a kosmotropic salt that is non-hazardous to humans.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of isolating RNA comprising the steps of:
   a) providing a sample comprising a mixture of RNA and DNA, wherein the sample is resuspended in an acidic binding solution comprising a kosmotropic salt at a concentration of less than or equal to about 1M;
b) contacting the sample with a solid support, wherein the RNA selectively binds to the solid support; and
c) isolating the RNA bound to the solid support.

2. The method of claim 1, wherein the kosmotropic salt is a salt formed from an anion selected from the group consisting of a sulfate $SO_4^{2-}$, a phosphate $HPO_4^{2-}$, an acetate $CH_3COO^-$, a hydroxide $OH^-$, a chloride $Cl^-$, and a formate $HCOO^-$.

3. The method of claim 1, wherein the concentration of the kosmotropic salt is 0.3M-0.9M.

4. The method of claim 1, wherein the binding solution has a pH ranging from 3 to 6.

5. The method of claim 1, further comprising washing the RNA bound to the support with a first wash solution comprising a kosmotropic salt at a concentration of less than or equal to about 1M, and then with a second wash solution having a pH ranging from 6 to 9.

6. The method of claim 5, wherein the first wash solution further comprises an alcohol.

7. The method of claim 5, wherein the first wash solution has the same composition as the acidic binding solution.

8. The method of claim 1, wherein the isolation of the RNA bound to the solid support requires elution of the RNA.

9. The method of claim 1, wherein the solid support is formed of a material selected from the group consisting of a silica, glass, silicon wafer, magnetic material, polystyrene, and metal plate.

10. The method of claim 1, wherein the solid support has a shape of a flat slide, pillar, bead, or sieve.

11. The method of claim 8, wherein the elution of the RNA requires an RNA-eluting solution comprising water or an aqueous solution comprising a salt concentration of 10 mM or less.

12. The method of claim 11, wherein the RNA-eluting solution has a pH ranging from 4 to 10.

13. The method of claim 1, wherein the RNA bound to the solid support comprises RNA of 200 nucleotides or less in length.

14. The method of claim 1, wherein the RNA molecule is a single stranded RNA molecule or a double stranded RNA molecule or a mixture of both.

15. A method of isolating RNA comprising the steps of:
a) providing a sample comprising a mixture of RNA and DNA, wherein the sample is resuspended in an acidic binding solution comprising a kosmotropic salt at a concentration of less than or equal to about 1M, wherein the pH of the acidic binding solution ranges from 3 to 6 and the kosmotropic salt does not comprise $Mg^{2+}$;
b) contacting the sample with a solid support, wherein the RNA selectively binds to the solid support; and
c) isolating the RNA bound to the solid support.

16. The method of claim 15, wherein the kosmotropic salt is a salt formed from an anion selected from the group consisting of sulfate $SO_4^{2-}$, a phosphate $HPO_4^{2-}$, an acetate $CH_3COO^-$, a hydroxide $OH^-$, a chloride $Cl^-$, and a formate $HCOO^-$.

17. The method of claim 15, wherein the solid support is formed of a material selected from the group consisting of a silica, glass, silicon wafer, magnetic material, polystyrene, and metal plate.

* * * * *

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: forward primer

<400> SEQUENCE: 1
yccakactcc tacgggaggc                                                   20

<210> SEQ ID NO 2
<211> LENGTH: 22
<212> TYPE: DNA
<213> ORGANISM: Artificial Sequence
<220> FEATURE:
<223> OTHER INFORMATION: reverse primer

<400> SEQUENCE: 2
gtattaccgc rrctgctggc ac                                                22
```